US006378376B1

(12) United States Patent
Derman et al.

(10) Patent No.: US 6,378,376 B1
(45) Date of Patent: Apr. 30, 2002

(54) ULTRASOUND TRANSDUCER MOUNTING ASSEMBLY

(75) Inventors: Richard Derman, Newton, PA (US); Shane Dunne; Aaron Fenster, both of London (CA)

(73) Assignee: Life Imaging Systems, Inc. (CA)

( * ) Notice: Subject to any disclaimer, the term of this patent is extended or adjusted under 35 U.S.C. 154(b) by 0 days.

(21) Appl. No.: 09/180,609

(22) PCT Filed: Mar. 20, 1998

(86) PCT No.: PCT/CA98/00248

§ 371 Date: Aug. 25, 1999

§ 102(e) Date: Aug. 25, 1999

(87) PCT Pub. No.: WO98/43234

PCT Pub. Date: Oct. 1, 1998

(Under 37 CFR 1.47)

Related U.S. Application Data

(60) Provisional application No. 60/041,344, filed on Mar. 21, 1997.

(51) Int. Cl.[7] .......................... G01N 29/00; A61B 8/12

(52) U.S. Cl. ............................ 73/606; 73/632; 73/633; 73/634; 73/639; 600/446

(58) Field of Search .......................... 73/606, 660, 663, 73/619, 620, 632, 633, 634, 635, 640, 866; 600/445, 659, 446, 447

(56) References Cited

U.S. PATENT DOCUMENTS

| | | | | | |
|---|---|---|---|---|---|
| 4,149,419 | A | * | 4/1979 | Connel, Jr. et al. | 73/639 |
| 4,398,425 | A | * | 8/1983 | Matzuk | 73/633 |
| 4,403,509 | A | * | 9/1983 | Kretz | 73/639 |
| 4,437,468 | A | * | 3/1984 | Sorenson et al. | 600/459 |
| 4,774,842 | A | * | 10/1988 | Kollar et al. | 73/640 |
| 5,454,371 | A | | 10/1995 | Fenster et al. | 128/660 |
| 5,511,429 | A | * | 4/1996 | Kosugi et al. | 73/151 |
| 5,562,095 | A | | 10/1996 | Downey et al. | 600/445 |

* cited by examiner

*Primary Examiner*—Hezron Williams
(74) *Attorney, Agent, or Firm*—Katten Muchin Zavis

(57) ABSTRACT

The present invention provides a mounting assembly, for use with an ultrasound transducer attached to an ultrasound machine, for determining the spacial relationship between a succession of 2D image slices of a target of a subject, generated by the ultrasound machine. The mounting assembly comprises: (i) means to mount an ultrasound transducer; (ii) means to engage a surface of the subject in the proximity of the target, the means to engage a surface being moveably attached to the means to mount an ultrasound transducer; and (iii) sensing means, in communication with the means to engage a surface, to measure the movement of the means to engage a surface during acquisition of the succession of 2D image slices. Preferably, the sensing means comprises a tilt sensor and a displacement sensor.

10 Claims, 2 Drawing Sheets

ULTRASOUND TRANSDUCER MOUNTING ASSEMBLY

This application claims benefit of Provisional application No. 60/041,344, filed Mar. 21, 1997.

BACKGROUND OF THE INVENTION

1. Field of the Invention

The present invention relates to the field of three-dimensional ultrasound imaging. More specifically, the present invention relates to an ultrasound probe mounting assembly.

2. Description of the Prior Art

Three-dimensional (3D) ultrasound imaging is a technique in which a set of spatially related two dimensional ultrasound slices (tomograms) of a target are collected and mathematically converted to create a virtual ultrasound volume. This virtual ultrasound volume facilitates the visualization of non-acquired slices of the target and a variety of rendered surfaces and projections of the target otherwise unobtainable using two-dimensional (2D) ultrasound imaging.

High fidelity 3D ultrasound requires, by definition, a data set in which the spacial relationship between the individual ultrasound slices is precisely known. High fidelity ultrasound is important for the accurate assessment of volumes and the appreciation of target geometry. The conventional method of choice for obtaining the precise spatial relationship between ultrasound slices is to actively constrain the position of each ultrasound slice. This is achieved by controlling the position of the ultrasound probe during generation of the slices by use of a motorized positioning device (mechanical scanning). Examples of 3D ultrasound imaging systems are described in detail in commonly assigned U.S. Pat. Nos. 5,454,371 (Fenster et al.) and 5,562,095 (Downey et al.), the contents of each of which are hereby incorporated by reference.

Although the mechanical scanning approach to 3D ultrasonography offers speed and accuracy, the bulkiness of the devices at times hinders the scan, particularly when imaging large structures. To overcome this problem, investigators have developed various "free-hand" acquisition techniques in which the operator can hold an assembly, composed of the transducer and an attachment (as will be discussed below, and manipulate the assembly over the subject to be imaged. A computer records the conventional 2D images generated by the ultrasound machine as well as their position and angulation. Because the geometric information about the transducer's location is not predefined, the exact relative position and angulation of the ultrasound transducer must be accurately known for each acquired image slice. This information is then used in the reconstruction of the 3D image in a manner that avoids distortions. Over the past two decades a number of free-hand scanning approaches have been developed which make use of three basic positioning techniques: acoustic; articulated arm; and magnetic field.

In acoustic position sensing, three sound emitting devices, such as spark gaps, are mounted on the transducer and an array of fixed position microphones are mounted above the patient. During scanning, the microphones continuously receive sound pulses from the transducer. The position and orientation of the transducer as each 2D image is acquired is determined by knowledge of the speed of sound in air and the time of flight of the sound pulses to the fixed microphones. This technique has a number of disadvantages, for example, the microphones must be placed over the patient in a way that provides unobstructed "lines-of-sight" to the sound emitters and sufficiently close to allow detection of the sound pulses. Further, the speed of sound varies with temperature and humidity and so, in a given environment, corrections must be made to avoid distortions in the 3D image.

One of the simplest approaches to free-hand scanning is to mount the transducer on a mechanical arm system with multiple moveable joints. Potentiometers located at the joints of the arms provide information about the relative movement of the arm during scanning. This system also has a number of disadvantages. For example, to avoid distortion in the final image, the potentiometers must be accurate and precise and the arm system must not flex. Sufficient accuracy may be achieved by keeping individual arms as short as possible and reducing the number of degrees of freedom. However, increased precision is achieved at the expense of flexibility in scanning and the size of the volume that can be imaged.

Magnetic position sensing makes use of a six degree-of-freedom magnetic field sensor to measure the ultrasound transducer's position and orientation. The approach makes use of a transmitter, which produces a spatially varying magnetic field, and a small receiver containing three orthogonal coils to sense the magnetic field strength. Although magnetic field sensors allow for less constrained geometrical tracking of the transducer, they are susceptible to noise and errors. For example, the devices are sensitive to electromagnetic interference form sources such as CRT monitors, AC power cables and ultrasound transducers.

It is an object of the present invention to provide an ultrasound transducer mounting assembly which allows for the determination of the spacial relationship between a succession of 2D image slices, which obviates and mitigates at least one of the disadvantages of the prior art.

SUMMARY OF THE INVENTION

Accordingly, in one of its aspects, the present invention provides a mounting assembly, for use with an ultrasound transducer attached to an ultrasound machine, for determining the spacial relationship between a succession of 2D image slices of a target of a subject, generated by the ultrasound machine, the mounting assembly comprising:

(i) means to mount an ultrasound transducer;

(ii) means to engage a surface of the subject in the proximity of the target, the means to engage a surface being moveably attached to the means to mount an ultrasound transducer; and (iii) sensing means, in communication with the means to engage a surface, to measure the movement of the means to engage a surface during acquisition of the succession of 2D image slices.

In another aspect, the present invention provides an ultrasound transducer assembly, for use with an ultrasound machine, for determining the spacial relationship between a succession of 2D image slices of a target of a subject, generated by the ultrasound machine, the ultrasound transducer assembly comprising:

(i) an ultrasound transducer;

(ii) assembly means mounted to the ultrasound transducer;

(iii) means to engage a surface of the subject in the proximity of the target, the means to engage a surface being moveably attached to the assembly means; and (iv) sensing means, in communication with the means to engage a surface, to measure the movement of the means to engage a surface during acquisition of the succession of 2D image slices.

Typically, the target to be scanned will be beneath the surface of the subject. Thus, the target may be an internal organ and the mounting assembly is translated over the skin of the patient. However, the present invention should not be limited in that sense.

Further, the "means to engage the surface of the subject" is intended to have a broad meaning in this specification. Specifically, as will be developed in more detail hereinbelow, this element can directly (e.g. wheel, roller, trackball,surface engaging tilt sensor and the like) or indirectly (e.g. non-surface engaging tilt sensor) engage the surface of the subject. Thus, the term "engage" is used to indicate that, in a notional sense, the element engages the surface of the subject to facilitate measurement of movement of the element by the sensing means.

BRIEF DESCRIPTION OF THE DRAWINGS

Embodiments of the present invention will be described, by way of example only, with reference to the accompanying drawings, in which.

DETAILED DESCRIPTION OF THE PREFERRED EMBODIMENTS

Figure 1:
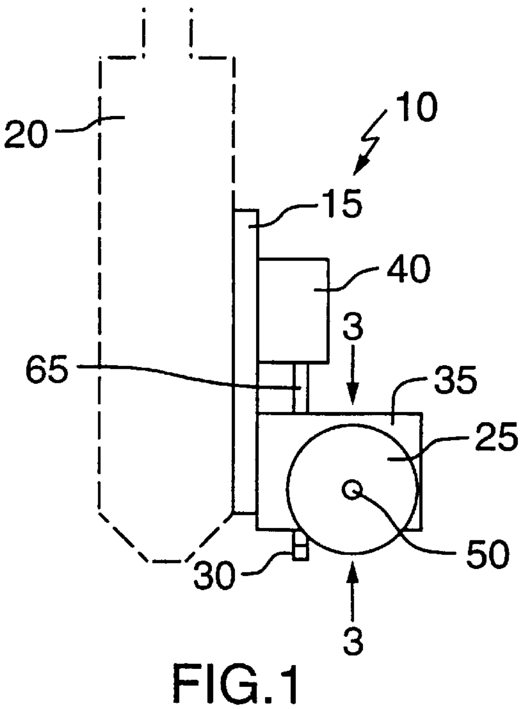
FIG. 1 shows a side view of a mounting assembly in accordance with the present invention.
Figure 2:
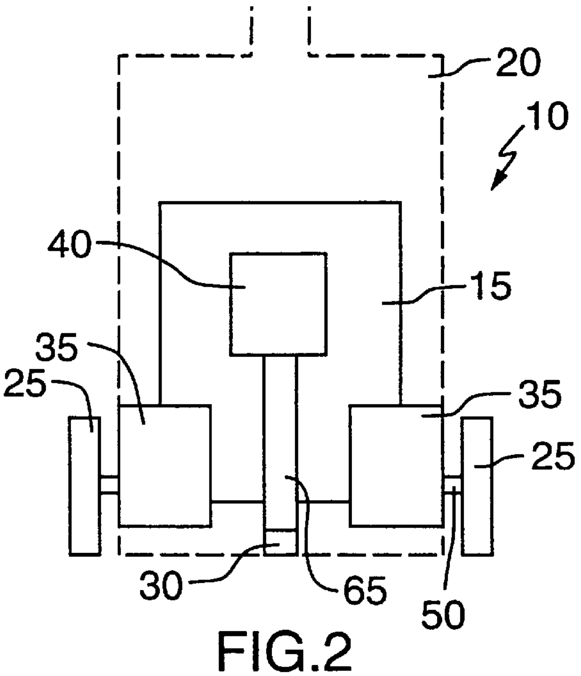
FIG. 2 shows a front view of the mounting assembly of claim 1.

A mounting assembly in accordance with one embodiment of the present invention is shown generally at 10 in FIGS. 1 and 2. Mounting assembly 10 comprises a means to securely mount an ultrasound transducer, such as mounting plate 15 (a mounted transducer is shown in outline 20) and at least one means to engage a surface, such as wheels 25 and/or plunger tip 30. Mounting assembly 10 further comprises at least one sensing means such as displacement sensor 35 and/or tilt sensor 40.

In the embodiment shown in the figures, wheels 25 are both moveably attached to mounting plate 15, each wheel being provided with a displacement sensor 35 to measure the rotation of each wheels 25 relative to the mounting plate as the mounting plate is moved across a surface of the target during ultrasound scanning.

Figure 3:
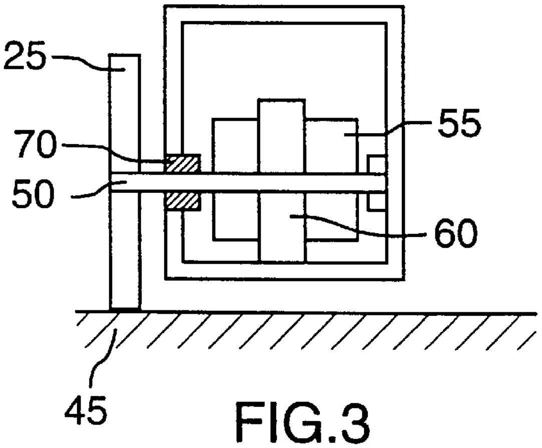
FIG. 3 shows a cross-section of the mounting assembly of FIG. 1 along the line 3—3.

The displacement sensor and wheel assembly is shown in FIG. 3. In the assembly, wheel 25 of known diameter rotates about an axis parallel to the surface 45 of a target (not shown) and perpendicular to the long axis of the ultrasound probe. Shaft 50 of wheel 25 passes through a shaft encoder 55 which is maintained stationary within displacement sensor 35 by encoder clamp 60. A seal 70 is provided where wheel shaft 50 enters displacement sensor 35 to prevent entry into the detector of contaminants. Wheels 25 may be removed from displacement sensor 35 to permit cleaning and replacement.

During the scanning of the target (not shown), transducer 20 (and thus, mounting assembly 10) is manipulated by the operator such that wheels 25 are held in light contact with surface 45 of the target (not shown), such that a no-slip condition is obtained as the transducer is translated across the surface of the target. As the transducer is translated, wheel 25 and, hence, shaft 50 rotates. Shaft encoder 55 provides a real-time output of the relative angular position of shaft 50, as shaft 50 rotates. Knowledge of the relative angular position of the shaft over time and the diameter of the wheels, allows an accurate determination of the relative movement of the transducer across the surface of the target during scanning.

As will be apparent, surface engaging means other than a pair of wheels are equally applicable for use in the displacement sensor assembly. For example, it is envisioned that a single wheel, a trackball (similar in operation to that in a computer mouse) and the like may be used in place of the pair wheels.

Using the translational information from the displacement sensor, it is possible to pin-point the relative position of the transducer at the time each individual 2D ultrasound slice is being acquired, i.e. the translational relationship between each successive 2D image slice can be determined.

Plunger tip 30 is moveably attached to mounting plate 15 by means of a tilt sensor 40. Tilt sensor 40 comprises a spring loaded plunger 65 and a means, such as a travel detector (not shown), to determine the position of the plunger in its stroke. Plunger 65 is positioned a fixed, known distance from the mounting plate (and hence, a fixed, known distance (d) from the transducer body). The tilt sensor is provided with a seal where the plunger enters travel detector to prevent entry into the travel detector of contaminants. Plunger 65 may be removed from the travel detector to permit cleaning and replacement.

The movement of the plunger and the calculation of the tilt angle are depicted in FIGS. 4A–4C and FIG. 5. For clarity, the mounting assembly shown in FIGS. 4A–4C and 5 is an embodiment in which displacement sensor 35 has been omitted.

As transducer 20 is tilted from a mean position perpendicular to the surface of the target (FIG. 4A), plunger 65 travels a distance relative to mounting plate 15 which is determined by the plungers distance from the centre of rotation of the transducer (d) and the tangent of the angle θ of the transducer's long axis relative to the normal to the surface of the target.

The means to determine the position of the plunger in its stroke is not particularly limited and may be any means which allows the travel of the plunger to be detected in real time. Examples of suitable means include potentiometic measurements (linear or rotary), use of a Linear Variable Differential Transformer (LVDT), optical sensing of a suitably encoded plunger and the like. Such determination means are conventional and the choice of a suitable device is within the purview of a person of skill in the art.

Further, it will be apparent that other means to measure the tilt of the transducer may be employed. For example, the tilt may be measured by means of a downward firing ultrasound range finder attached to the transducer, which measures the distance from this range finder to the surface of the target by measuring the reflected ultrasound signal.

Figures 4A, 4B, 4C:
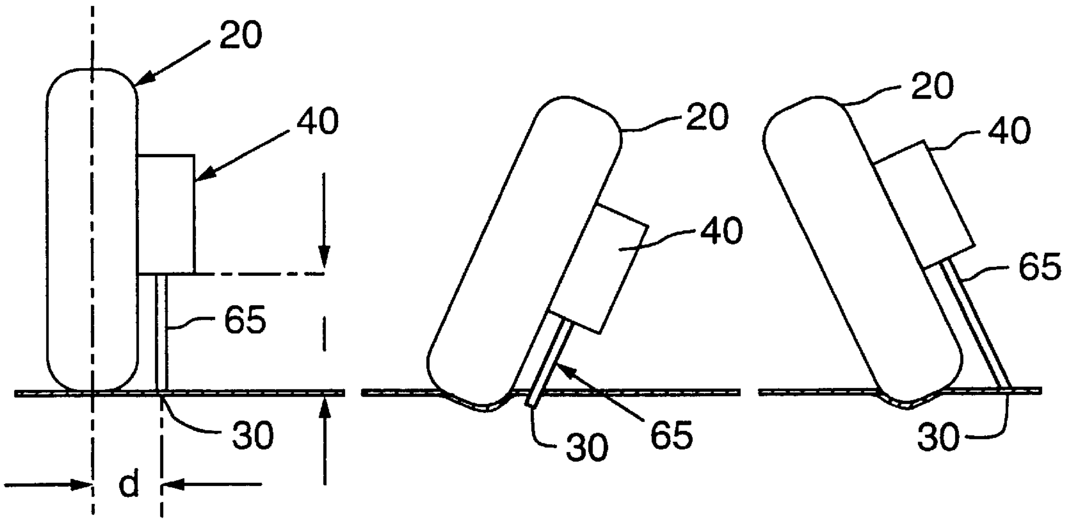
FIGS. 4A, 4B and 4C show the operation of a tilt detector on the mounting assembly.
Figure 5:
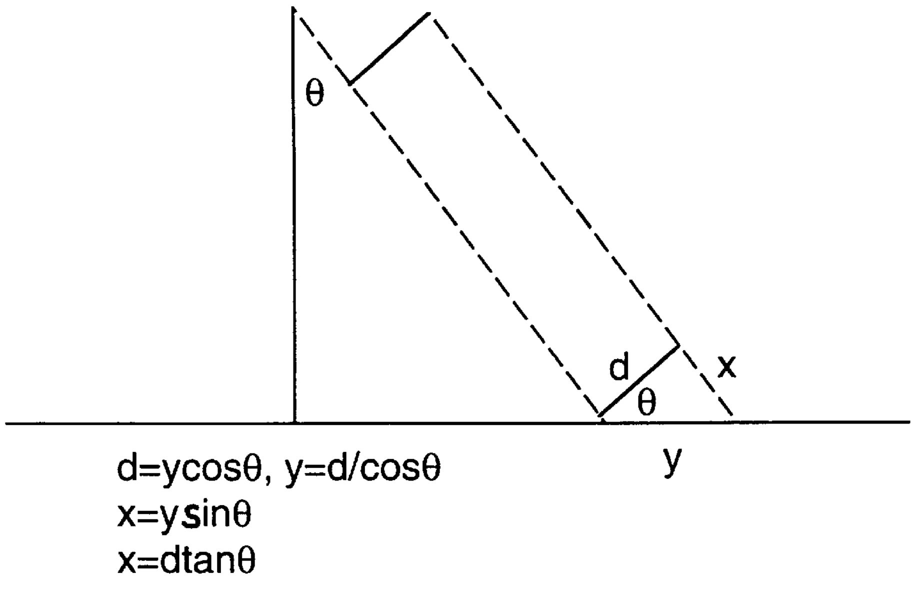
FIG. 5 is a representation of the geometry used to calculate the tilt angle of the mounting assembly.

As stated above, in the embodiment of the present invention shown in FIGS. 4A–4C, the mounting assembly is only provided with a single tilt sensor and no displacement sensor. This embodiment may be effectively used to determine the spacial relationship between successive 2D scans in situations where there is no translation of the transducer on the surface of the target. This type of 2D image acquisition is known as "fan" scanning which is well known to ultrasound practitioners and as such, it will not be described in detail herein. More information on fan scanning may be found in, for example, commonly assigned U.S. Pat. No. 5,454,371 and Fenster et al., *IEEE Engineering in Medicine and Biology*, 15, 41–52 (1996), the contents of each of which are hereby incorporated by reference.

More complex fan scanning, which includes rocking the transducer about an axis perpendicular to the fanning axis, may be accommodated by utilizing a mounting assembly comprising a pair of tilt sensors which are mounted to the mounting plate such that they are displaced equal lateral distances form the long axis of the ultrasound transducer. In this application, the difference in the travel of each plunger will be proportional to the amount of rocking and the average of the plunger travel will provide the amount of tilt. It is envisioned that this type of application will be particularly useful for transducers which have azimuthally curved surface contact profiles, such as convex arrays and mechanical sector scanners.

It is also envisioned that a mounting assembly may only be provided with displacement sensors, i.e., with no tilt sensors. This type of assembly may be used for simple translations where the transducer is held normal to the surface of the target at all times. In this respect, a mounting assembly may be provided with only a single displacement sensor/wheel assembly if a linear scan path is to be followed. The provision of two separate displacement sensors, spaced a known distance either side of the central axis of the transducer (as depicted in FIGS. 1 and 2), will permit the user to compensate for slight deviations form a linear scan path, where one wheel has travelled a known distance further than the second wheel.

Although the present invention has been described with reference to a mounting assembly comprising at least one surface engaging displacement sensor and/or a surface engaging tilt sensor, it is envisioned that a mounting assembly may also comprise a surface engaging displacement sensor in combination with a non-surface engaging tilt sensor. An example of a suitable non-surface engaging tilt sensor is a Series 500, 700 or 900 precision tiltmeter manufactured by Applied Geomechanics of Santa Cruz, Calif.

All the embodiments herein have been described with reference to a mounting means to which a transducer may be securely attached. However, the scope of the present invention is not limited to the use of a flat mounting plate as shown in the figures which may be attached to the transducer by a fastening means such a screws, clips or adhesive. For example, the mounting means may comprise a cage structure into which a transducer may be placed or a trolley structure having a spring-clip arrangement for holding a transducer firmly in place.

Typically, an ultrasound transducer is mounted on the present mounting assembly to yield an ultrasound transducer assembly. The ultrasound transducer may then be connected to a computer equipped with a video display, and thereafter translated over the surface of the target to be scanned.

Thus, in use, the positional information from the displacement and tilt sensors will be sent directly to the computer in which the three-dimensional image reconstruction will take place, i.e. the information is not necessarily sent to the ultrasound machine itself. The positional information will be stored in association with the succession of digitized two-dimensional image slices and utilized during the three-dimensional image reconstruction. In a presently preferred embodiment, the positional information will form part of a positional information file which is used during the image reconstruction.

The reconstruction technique for producing a three-dimensional image based on free-hand scanning requires three spacial coordinates and the three angles describing the orientation of the transducer. Such reconstruction techniques are known in the art and are described in, for example, Detmer et al., *Ultrasound in Medicine and Biology*, 20, 923–936 (1994) and Ohbuchi et al., *SPIE-Visualization in Biomedical Computing*, 1801, 312–323, (1992), the contents of each of which are hereby incorporated by reference. In an embodiment where not all the information is available, (e.g., not angular information) then an assumption is made. For example, if no angular information is available, an assumption is made that the transducer was moved across the surface of the subject without tilting, resulting in the use of arbitrary but constant angles in the reconstruction algorithm. If no displacement information is available and the transducer is held stationary on the surface, then it is assumed that the transducer was not moved over the surface of the target (e.g. in most cases, the skin surface).

While this invention has been described with reference to illustrative embodiments, this description is not intended to be construed in a limiting sense. Various modifications of the illustrative embodiments as well as other embodiments will be apparent to persons of skill in the art. It is therefore contemplated that the appended claims will cover any such modifications or embodiments.

What is claimed is:

1. A mounting assembly, for use with an ultrasound transducer attached to an ultrasound machine, for determining the spacial relationship between a succession of 2D image slices of a target of a subject, generated by the ultrasound machine, the mounting assembly comprising;

(i) a mounting structure for a transducer, said mounting structure comprising a flat plate, cage or trolley structure;

(ii) a wheel or plunger tip movably attached to the mounting structure in a forward position, said wheel or plunger engaging the surface of a subject in the proximity of the target; and (iii) displacement or tilt sensor in communication with one or both of said wheel or plunger to measure movement of the wheel or plunger during acquisition of the succession of 2D image slices, wherein said mounting assembly is an independent hand held assembly.

2. A mounting assembly according to claim 1, wherein the tilt sensor comprises a plunger having a plunger tip as the surface engaging means.

3. A mounting assembly according to claim 2, wherein the tilt sensor further comprises a means to determine the travel of the plunger in its stroke.

4. A mounting assembly according to claim 1, wherein the displacement sensor comprises a shaft encoder to provide an output of the relative angular position of the wheel.

5. A mounting assembly according to claim 1, the sensing comprises both a tilt sensor and a displacement sensor.

6. A mounting assembly, for use with an ultrasound transducer attached to an ultrasound machine, for determining the spacial relationship between a succession of 2D image slices of a target of a subject, generated by the ultrasound machine, the mounting assembly comprising;

(i) an ultrasound transducer mounted to a mounting structure comprising a flat plate, cage or trolley structure;

(ii) a wheel or plunger tip movably attached to the mounting structure in a forward position, said wheel or plunger engaging the surface of a subject in the proximity of the target; and (iii) displacement or tilt sensor in communication with one or both of said wheel or plunger to measure movement of the wheel or plunger during acquisition of the succession of 2D image slices.

7. A mounting assembly according to claim 6, wherein the tilt sensor comprises a plunger having a plunger tip as the surface engaging means.

8. An ultrasound transducer assembly according to claim 7, wherein the tilt sensor further comprises a means to determine the travel of the plunger in its stroke.

9. A mounting assembly according to claim 6, wherein the displacement sensor comprises a shaft encoder to provide an output of the relative angular position of the wheel.

10. An ultrasound transducer assembly according to claim 6, wherein the sensing means comprises both a tilt sensor and a displacement sensor.

* * * * *